(12) United States Patent
Cattadoris et al.

(10) Patent No.: US 8,177,082 B2
(45) Date of Patent: May 15, 2012

(54) FLEXIBLE MEMBRANE VALVE FOR CELL CULTURE VESSEL

(75) Inventors: Henry Joseph Cattadoris, Scarborough, ME (US); Gregory Roger Martin, Acton, ME (US); Allison Jean Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 756 days.

(21) Appl. No.: 12/148,321

(22) Filed: Apr. 18, 2008

(65) Prior Publication Data

US 2009/0263893 A1    Oct. 22, 2009

(51) Int. Cl.
*B65D 53/00* (2006.01)
*C12M 1/24* (2006.01)
*C12M 3/00* (2006.01)

(52) U.S. Cl. ..... 215/270; 215/248; 215/261; 435/297.1; 435/303.1; 435/304.1; 435/304.3; 435/305.1; 435/305.4; 435/307.1; 251/213; 251/294; 251/298; 251/336

(58) Field of Classification Search ............... 435/297.1, 435/303.1, 304.1, 304.3, 305.1, 305.4, 307.1; 251/213, 294, 298, 336; 215/248, 261, 270
See application file for complete search history.

(56) References Cited

U.S. PATENT DOCUMENTS

| | | | |
|---|---|---|---|
| 4,420,094 A | 12/1983 | Chapin | 220/37 |
| 4,839,292 A | 6/1989 | Cremonese | |
| 5,108,001 A | 4/1992 | Harris | 220/203 |
| 5,258,243 A | 11/1993 | Cannone | 429/55 |
| 6,027,694 A | 2/2000 | Boulton et al. | 422/102 |
| 6,261,267 B1 | 7/2001 | Chen | 604/247 |
| D446,419 S | 8/2001 | Ming-Shiue | D7/392.1 |

(Continued)

FOREIGN PATENT DOCUMENTS

DE    2541000    11/1976

(Continued)

OTHER PUBLICATIONS

Petaka User's Guide, 2004 Copyright.

(Continued)

*Primary Examiner* — Nathan Bowers
(74) *Attorney, Agent, or Firm* — Susan S. Wilks

(57) ABSTRACT

An assembly for culturing cells includes a housing defining a reservoir for containing cell culture media and an opening in fluid communication with the reservoir. The cell culture assembly further includes a filter valve assembly configured to sealingly engage the opening. The filter valve assembly includes a flexible membrane, a contiguous side wall, an end wall, and a microbial filter. The end wall has an opening and extends across one end of the side wall to form a major cavity within the side wall and the end wall. The flexible membrane has a slit spanning the membrane and is disposable within the major cavity such that the membrane sealingly divides the major cavity into (i) a chamber formed between the end wall and the membrane and (ii) a minor cavity formed by the membrane and a portion of the side wall. The minor cavity is in fluid communication with the reservoir. The slit is biased in a closed position to prevent fluid from passing from the minor cavity into the chamber and is configured to open to allow gas to pass from the minor cavity into the chamber when the pressure differential across the membrane is above a threshold. The filter is disposed between the membrane and the opening such that air flowing through the opening in the end wall into the chamber passes through the filter.

19 Claims, 15 Drawing Sheets

U.S. PATENT DOCUMENTS

| | | | |
|---|---|---|---|
| 6,341,718 B1* | 1/2002 | Schilthuizen et al. | 222/207 |
| 6,699,118 B1 | 3/2004 | Wahner et al. | 454/20 |
| 2001/0055803 A1 | 12/2001 | Wall et al. | 435/294.1 |
| 2002/0039785 A1 | 4/2002 | Schroeder et al. | |
| 2002/0084294 A1 | 7/2002 | Paulovich et al. | 222/482 |
| 2004/0005699 A1* | 1/2004 | Roos et al. | 435/297.5 |
| 2004/0029266 A1 | 2/2004 | Barbera-Guillem | 435/297.5 |
| 2004/0173258 A1 | 9/2004 | Stein et al. | 137/68.19 |
| 2005/0074873 A1* | 4/2005 | Shanler et al. | 435/304.3 |
| 2005/0145634 A1 | 7/2005 | Giblin et al. | 220/580 |
| 2007/0042704 A1 | 2/2007 | Qualy et al. | 454/250 |
| 2008/0160502 A1* | 7/2008 | Barnes et al. | 435/4 |
| 2009/0148941 A1* | 6/2009 | Florez et al. | 435/325 |
| 2010/0136686 A1* | 6/2010 | Wilson | 435/374 |

FOREIGN PATENT DOCUMENTS

| | | |
|---|---|---|
| EP | 0 337 677 | 4/1989 |
| EP | 1514919 | 3/2005 |
| FR | 2677664 | 12/1992 |
| WO | 88/01605 | 3/1988 |
| WO | 2004/092034 | 10/2004 |

OTHER PUBLICATIONS

Corning RoboFlask Cell Culture Vessels, 2005 Copyright.
OptiCell 2100 Max Cell Culture System Quick Start Guide Copyright 2004.
Corning HYPERFlask Cell Culture Vessels, 2007 Copyright.
Corning CellSTACK Culture Chambers 2007 Copyright.

* cited by examiner

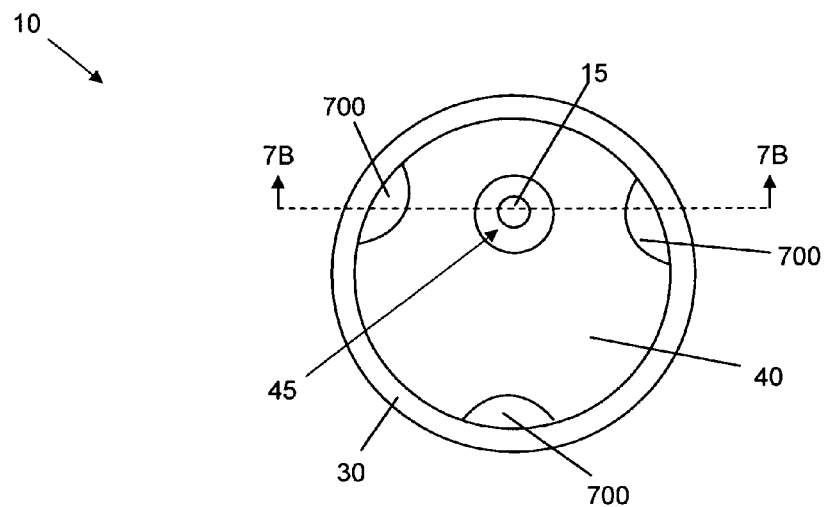
FIG. 7A
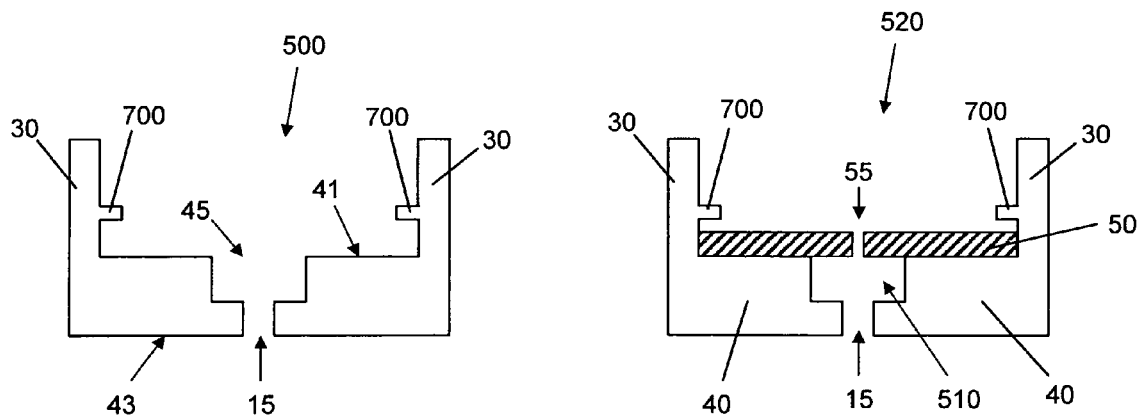
FIG. 7B
FIG. 7C

FLEXIBLE MEMBRANE VALVE FOR CELL CULTURE VESSEL

FIELD

The present disclosure relates to vessels for culturing cells and to valves for use in closed vessels, particularly to valves for releasing pressure.

BACKGROUND

Air handling in cell culture vessels with little or no headspace is problematic. Some cell culture vessels designed to be filled entirely or nearly entirely with liquid culture medium have caps that seal to prevent leaking. However, as the vessel experiences, for example, temperature swings, gas and vapor pressure changes in the vessel can lead to distortion of the vessel and decrease integrity of the vessel. Accordingly, it would be desirable to provide a vent for such systems. Such vents should include a microbial filter to prevent contaminated air from entering the cell culture environment. However, such vents do not work properly when wet and it is difficult to keep the filters dry in systems with limited headspace.

BRIEF SUMMARY

The present disclosure provides a vent assembly for cell culture systems. The vent assembly is effective in limited headspace systems designed to be completely or nearly completely filled with cell culture medium.

In an embodiment, the disclosure provides an assembly for culturing cells. The assembly includes a housing defining a reservoir for containing cell culture media and an opening in fluid communication with the reservoir. The cell culture assembly further includes a filter valve assembly configured to sealingly engage the opening. The filter valve assembly includes a flexible membrane, a contiguous side wall, an end wall, and a microbial filter. The end wall has an opening and extends across one end of the side wall to form a major cavity within the side wall and the end wall. The flexible membrane has a slit spanning the membrane and is disposed within the major cavity such that the membrane sealingly divides the major cavity into (i) a chamber formed between the end wall and the membrane and (ii) a minor cavity formed by the membrane and a portion of the side wall. The minor cavity is in fluid communication with the reservoir. The slit is biased in a closed position to prevent fluid from passing from the minor cavity into the chamber and is configured to open to allow gas (including vapor) to pass from the minor cavity into the chamber when the pressure differential across the membrane is above a threshold. The filter is disposed between the membrane and the opening such that air flowing through the opening in the end wall into the chamber passes through the filter.

In an embodiment, the disclosure provides a vent cap assembly for a cell culture apparatus. The assembly includes a cap housing member having a generally cylindrical side wall and an end wall extending across one end of the side wall to form a major cavity within the cylindrical side wall and the end wall. The end wall has a first major surface facing the major cavity, an opposing second major surface, and an opening extending through the end wall from the first major surface to the second major surface. The assembly further includes a flexible membrane having first and second opposing major surfaces and a slit extending through the membrane from the first major surface to the second major surface. The membrane is disposable within the major cavity such that the membrane sealingly divides the major cavity into (i) a chamber formed between the first major surface of the end wall and the first major surface of the membrane and (ii) a minor cavity formed by the second major surface of the membrane and a portion of the side wall. The slit is biased in a closed position to prevent fluid from passing from the minor cavity into the chamber and is configured to open to allow gas (including vapor) to pass from the minor cavity into the chamber when the pressure differential across the membrane is above a threshold. The assembly may also include a microbial filter disposed between the membrane and the opening such that air flowing through the opening in the end wall into the chamber passes through the filter.

One or more of the various embodiments presented herein provide one or more advantages over vent assemblies or culture apparatuses, particularly those intended have limited headspace. For example, the vent assemblies and culture vessels described herein allow for release of gasses or vapor when internal pressure within increases to prevent distortion of the vessel. The vent assemblies and culture vessels also allow release of such gasses and vapor in vessels with limited headspace, while preventing wetting of a microbial filter. As such, concerns regarding subjecting the vessel to an environment at a first temperature and then to an environment at a second temperature may be reduced. These and other advantages will be readily understood from the following detailed descriptions when read in conjunction with the accompanying drawings.

BRIEF DESCRIPTION OF THE DRAWINGS

FIGS. 3A-B are side views and FIG. 3C is a head on view along line 3C of FIG. 3B.

FIG. 5B includes a membrane, and FIG. 5C includes a membrane and a filter.

FIG. 7A is a schematic diagram of a top down view of a vent cap housing member looking into a cavity formed by a side wall and end wall of the housing member.

FIG. 7B is a schematic diagram of a cross section of the vent cap housing member shown in FIG. 7A taken along line 7B-7B.

FIG. 7C is a schematic diagram a cross section of the vent cap housing member shown in FIG. 7B with a membrane.

FIG. 12A showing portions of a housing; FIG. 12B includes a membrane; and FIG. 12C includes a filter.

Figure 1:
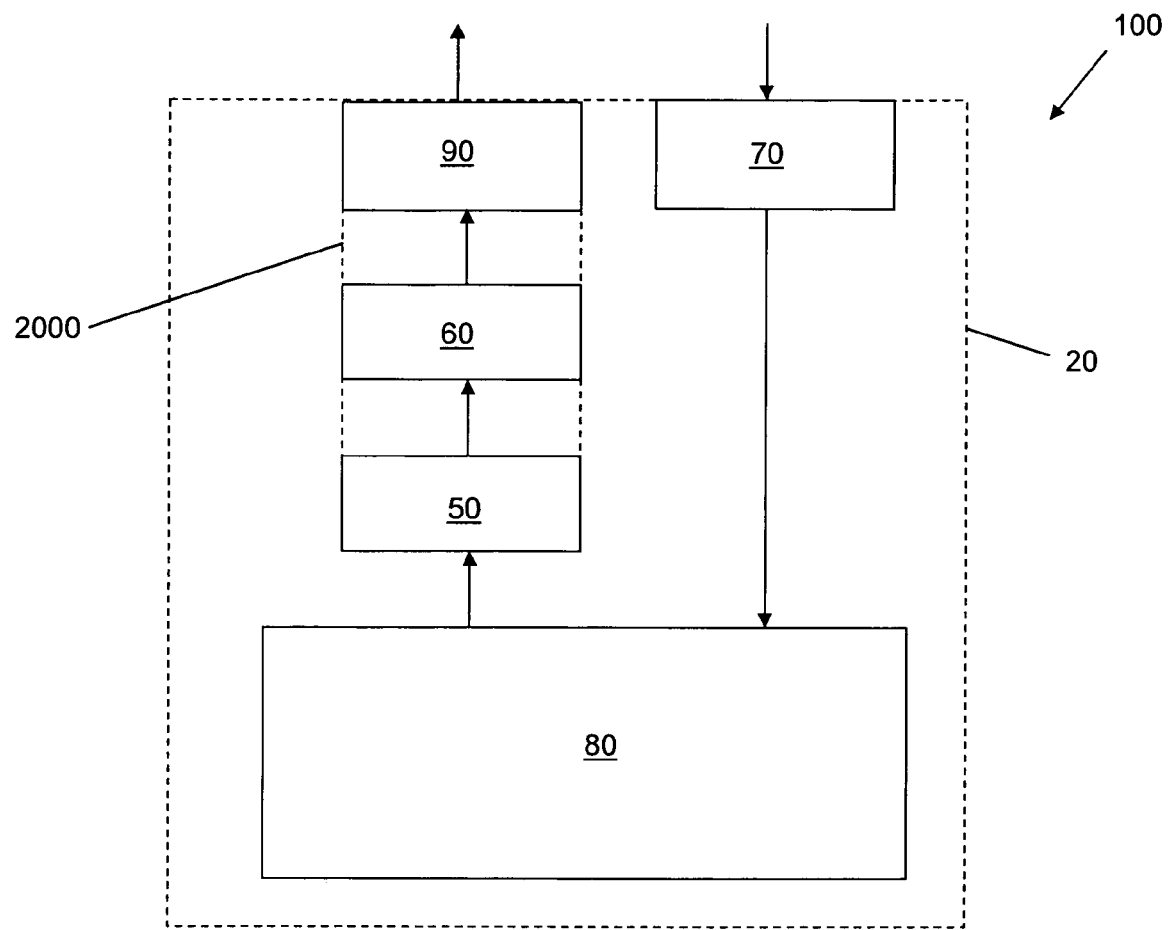
FIGS. 1-2 are schematic block diagrams of representative components of cell culture vessels having vent valve assemblies.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The present disclosure describes, inter alia, cell culture vessels or vent caps having valve assemblies that may be used in cell culture environments with limited head space. The vent assemblies described herein, in various embodiments, allow for release of gas and vapor from a reservoir of a cell culture vessel when pressure builds within the reservoir and generally prevent liquid culture medium from leaking through the valve assembly or vent cap.

Nearly any cell culture vessel can be adapted for use with the valve assemblies or vent caps described herein. Examples of suitable cell culture vessels for use with the valve assemblies or vent caps described herein include flasks, roller bottles, perfusion chambers, bioreactors, and fermenters. Some commercially available cell culture vessels that may be readily adapted to include a vent assembly or vent cap as described herein include the PETAKA™ Cell Culture vessel, (Celartia, Ltd.), CELL STACK™ culture chambers (Corning, Inc.), HYPERFLASK™ cell culture chambers (Corning, Inc.), ROBOFLASK™ cell culture chambers (Corning, Inc.), and OPTICELL™ cell culture systems (Nunc International). The greatest benefit will likely be achieved by closed system cell culture vessels with little or no headspace where internal pressure may change, such as with a change in temperature, a change in volume, e.g. as with an addition or withdrawal of cell culture medium, etc.

Figure 2:
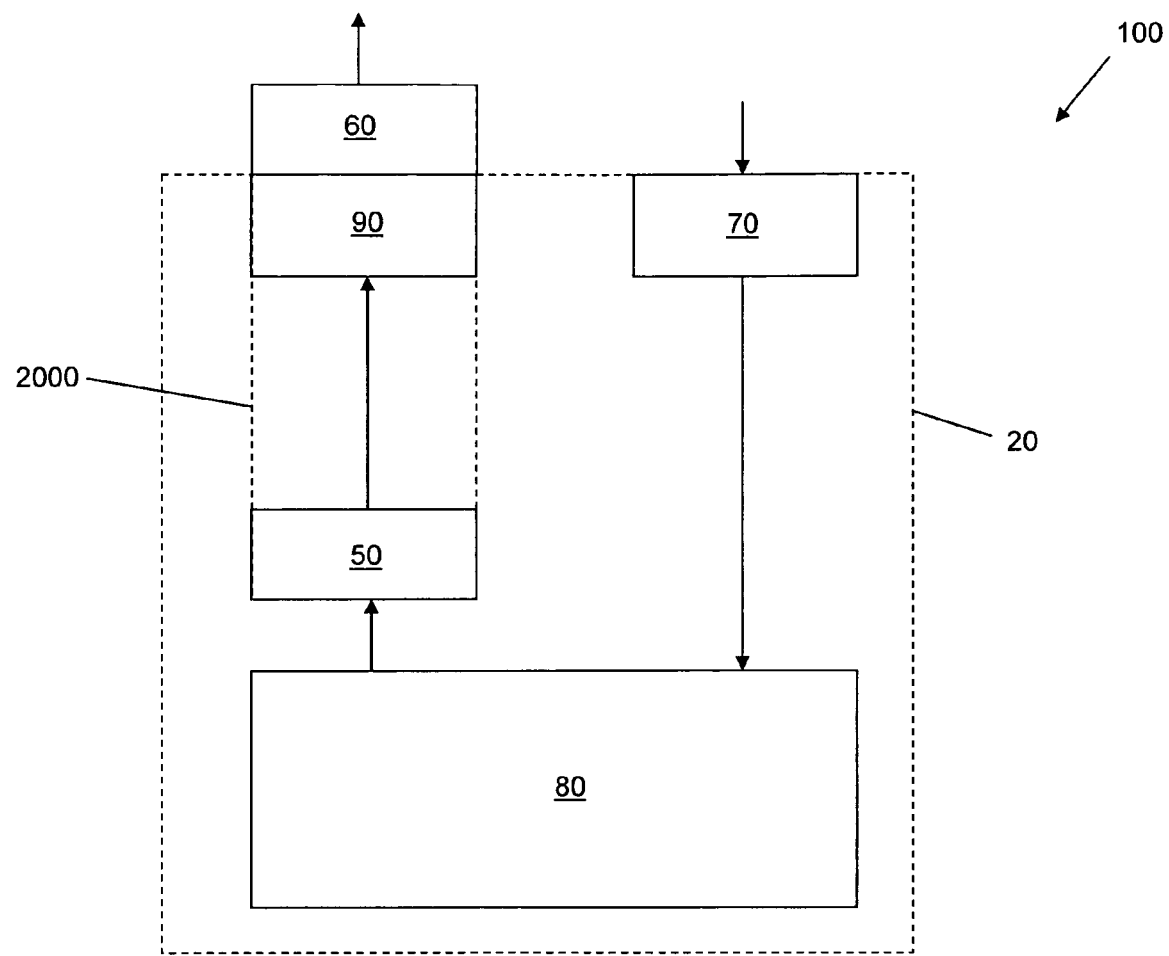

Referring to FIGS. 1-2, block diagrams of some components of various embodiments of cell culture vessels 100 having valve assemblies 2000 are shown. The arrows depicted in FIGS. 1-2 indicate a direction of fluid (e.g., gas or liquid) flow for purposes of discussion. The depicted cell culture vessels 100 have a housing 20 defining a reservoir 80 and an opening or outlet 90 in fluid communication with the reservoir 80. The depicted cell culture vessels 100 may also include an inlet 70 in fluid communication with the reservoir 80. Cell culture fluid, cells, or the like may be introduced into the reservoir 80 via the inlet 70. In various embodiments, the inlet 70 and outlet 90 are formed by the same opening defined by housing 20 (embodiment not shown in FIGS. 1-2). The vessel 100 also includes a valve assembly 2000 that sealingly engages the opening or outlet 90 formed in housing 20 to prevent fluid from exiting the reservoir via the opening. For example, the valve assembly 2000, or portions thereof may be integrally formed from the housing 20.

The valve assembly 2000 includes a flexible membrane 50 and a microbial filter 60. The membrane 50 contains a slit (not shown in FIGS. 1-2) that is biased in a closed position to prevent liquid culture medium from exiting the reservoir 80, for example when the vessel 100 is inverted such that liquid is pressed against the membrane. The slit is configured to open to allow gas to exit the reservoir 80 via the opening or outlet 90 when the pressure differential across the membrane 50 is above a threshold, for example when internal pressures might otherwise distort housing 20 or reservoir 80. Of course, the threshold at which the slit opens may be lower that that which would distort housing 20 or reservoir 80. Preferably, the pressure differential threshold at which the slit opens is above a pressure of inverted liquid on the membrane 50 and below a pressure that could distort or compromise the integrity of housing 20 or reservoir 80. It will be understood that the specific pressure differential will be related to the geometry of the vessel. For example, in the Corning HYPERFLASK™ the slit may be configured to open at a pressure differential across the membrane of greater than about 0.25 psi, but less than 0.5 psi. The filter 60 is positioned such that air that may flow through the outlet 90 into the reservoir 80 (e.g., when internal pressure is lower than external pressure by an amount that meets or exceeds the threshold) passes through the filter 60. For example, the filter 60 may be disposed between the membrane 50 and the outlet 90 (see, e.g., FIG. 1) or exterior to the housing 20 and covering the opening or outlet 90 (see, e.g., FIG. 2). It will be understood that the amount that the slit opens may vary according to the pressure differential across the membrane 50 and that the slit may, in certain situations, only be partially open to provide for sufficient venting.

Figure 3A:
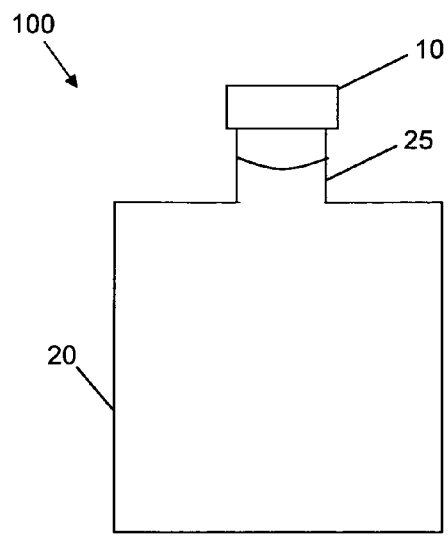
FIGS. 3A-C are schematic diagrams of cell culture vessels with a vent cap.
Figure 3C:
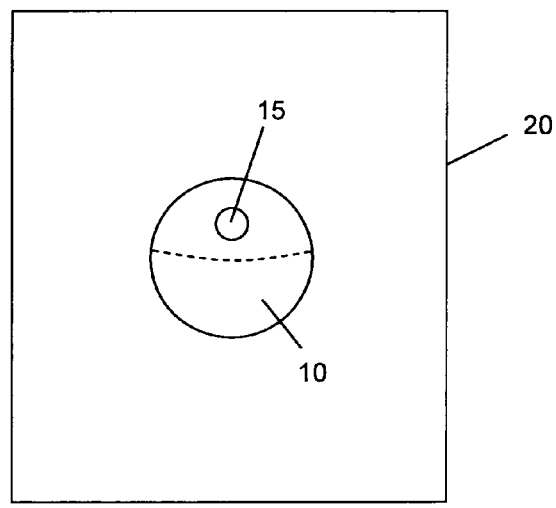
Figure 3B:
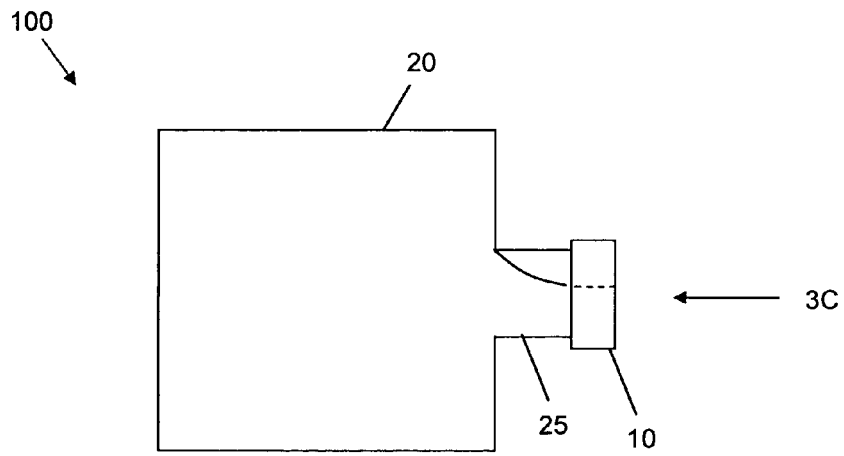

Referring now to FIG. 3, schematic drawings of various views of a cell culture vessel 100 having a vent cap 10 are shown. In the depicted embodiment, the cell culture vessel 100 contains a housing 20 forming a neck 25. The vessel 100 is filled with culture medium up to the neck region 25 and is configured to be laid with the neck 25 horizontal for purposes of culturing (see, e.g., FIG. 3B). Accordingly, cap 10 is configured to sealingly engage neck 25. For example, cap 10 may be internally threaded and neck 25 may be externally threaded to allow cap 10 to be screwed onto neck 25. FIG. 3C is a head-on view of vessel 100 and cap 20 along the line 3C of FIG. 3B. As shown in FIG. 3C, the cap has an opening 15 for venting that is off center so that the opening can be positioned above the level of the culture medium (depicted by dashed line). Accordingly, when pressure builds within the vessel 100, gas and vapor, rather than liquid, can be vented through the opening 15 in the cap 10.

Figure 4A:
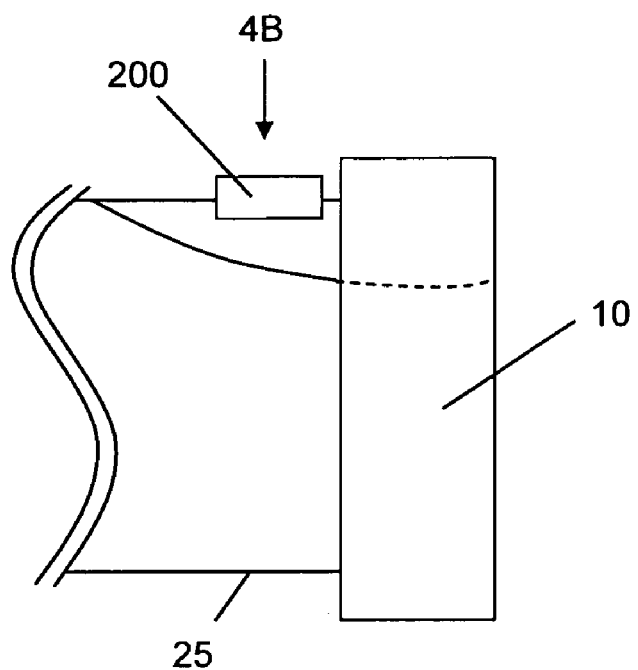
FIG. 4A is a schematic diagram of a close-up side view of a neck portion of a cell culture vessel having a valve assembly.
Figure 4B:
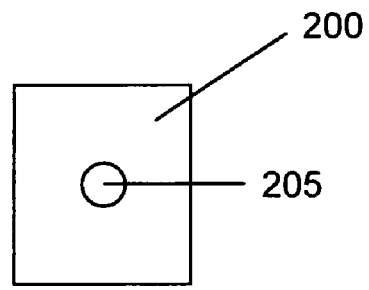
FIG. 4B is a schematic diagram of a valve assembly taken along line 4B of FIG. 4A.

Referring to FIG. 4, views of an alternative embodiment of the vessel 100 depicted in FIG. 3 are shown. In FIG. 4A, the neck portion 25 of the vessel is shown, and a vent assembly 200 is disposed in the neck 25. FIG. 4B is a head-on view of the vent assembly 200 along the line 4B in FIG. 4A. The vent assembly 200 has an opening 205 for venting. The vent assembly 200, or at least a portion thereof, is positioned in the neck 25 such that the assembly 200, or a portion thereof, is not in contact with culture medium. Accordingly, when pressure builds within the vessel 100, gas and vapor, rather than liquid, can be vented through the opening 15 in the vent assembly 200.

Figure 5A:
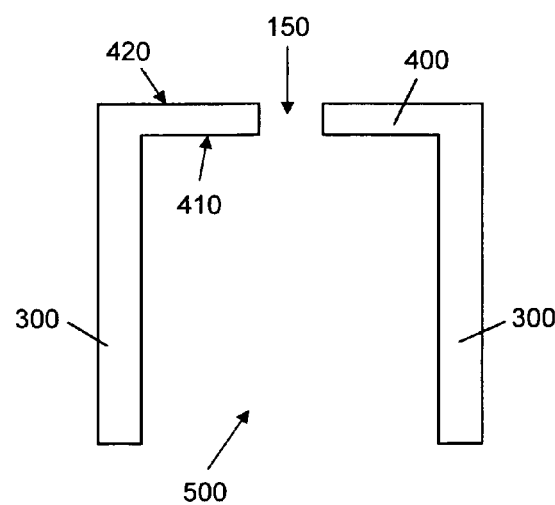
FIGS. 5A-C are schematic diagrams of cross-sections of a valve assembly.
Figure 5B:
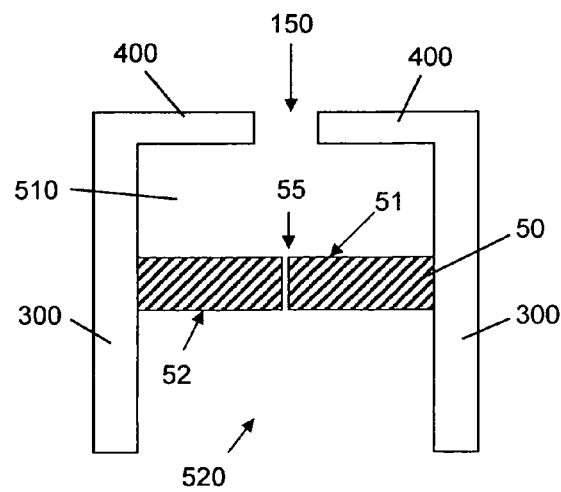
Figure 5C:
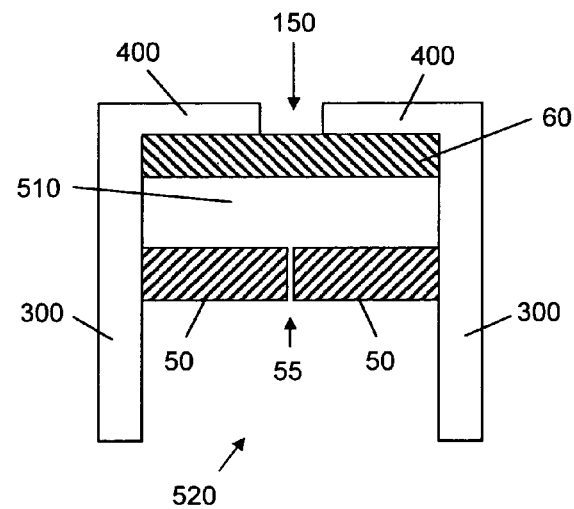

Referring now to FIG. 5, schematic diagrams of cross-sectional views of a vent assembly, which may be a vent cap as shown in FIG. 3 or an assembly as shown in FIG. 4, are shown. FIG. 5A shows a cross-section of a contiguous side wall 300 and an end wall 400 extended across one end of the side wall 300 to form a major cavity 500 within the side wall 300 and end wall 400. The end wall 400 has a first major surface 410, facing the major cavity 500, and an opposing major surface 420. An opening 150 extends through the end wall 400. In FIG. 5B, a flexible membrane 50 is disposed within the major cavity 520 and sealingly divides the major cavity into a chamber 510 and a minor cavity 520. The chamber 510 is formed between a first major surface 51 of the membrane 50, the first major surface 410 of the end wall 400, and a portion of the side wall 300. The minor cavity 520 is formed by a second major surface 52 of the membrane 50, which surface 52 opposes the first major surface 51, and a portion of the side wall 300. A slit 55 extends through the membrane 50 from the first major surface 51 to the second major surface 52. The slit 55 is biased in a closed position to prevent fluid (e.g., gas or liquid) in minor cavity 520 from entering chamber 510 and exiting opening 150. As pressure builds within minor cavity 520, relative to chamber 510, the flexible membrane 50 is capable of distending and allowing the slit 55 to open to vent gas from the minor cavity 520 into chamber 510 and out opening 150. As shown in FIG. 5C, a microbial filter 60 is positioned such that air flowing into chamber 510 via opening 150 is filtered. The filter 60 is desirable to prevent contaminated air flowing into opening 150 from reaching the reservoir of a cell culture vessel. For example, in situations where pressure within the minor cavity 520 drops, relative to chamber 510, causing membrane to distend and allowing slit 55 to open to allow air to enter the minor cavity 520.

It will be understood that slit 55 is shown as open in FIGS. 5B-C for purposes of illustration and that slit 55 is biased towards being closed and is configured to open when a sufficient pressure differential exists across the membrane 50. Slit 55 is also shown as being open for purposes of illustration in FIGS. 7C, 8D, 9D, 10B-C, and 11B-C.

Referring now to FIGS. 6-11, various embodiments of vent cap assemblies are shown. The depicted vent cap assemblies have cap housing members 10 that include a side wall 30 and an end wall 40 extending across one end of the side wall 30 forming a major cavity 500. An opening 15 for venting is formed in the end wall 40. The vent cap assemblies also contain a microbial filter 60 and a membrane 50. While not shown, it will be understood that the side walls 30 may contain internal threads for screwing onto an externally threaded portion of a cell culture vessel or may contain any other suitable mechanism for sealingly engaging an opening of a cell culture vessel. The depicted vent cap assemblies have generally cylindrical side walls 30. However, it will be understood that the side wall 30 may be formed in any suitable shape. The shape of the internal surface of the side wall 30 in many embodiments is determined by the shape of the opening, neck portion, or other region of a cell culture vessel that the vent cap assembly is configured to engage.

Figure 6:
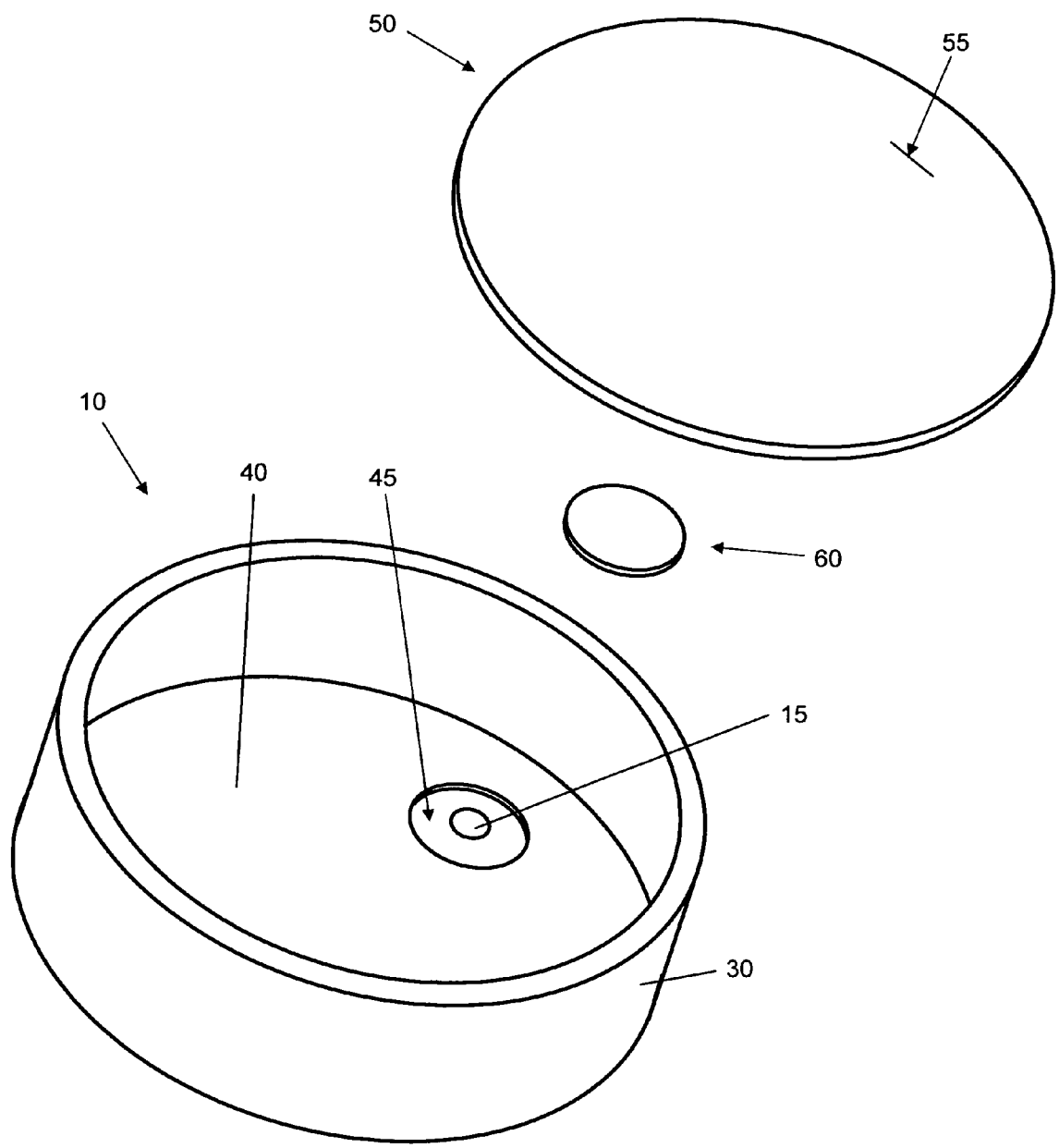
FIG. 6 is a schematic diagram of an exploded perspective view of a vent cap assembly.

FIG. 6 is a schematic diagram of an exploded view of a representative vent cap assembly. The depicted cap housing member 10 contains a counter bore 45 on an internally facing surface of the end wall 40. As shown in, e.g. FIGS. 7-8, a microbial filter 60 may be seated in the counter bore 45. The counter bore 45 may alternatively or additionally serve to provide space for the membrane 50 to expand and allow the slit 55 to open for gas to pass out the opening 15. The vent cap housing member 10 shown in FIG. 7 is similar to that shown in FIG. 6, except that the cap housing member 10 depicted in FIG. 7 includes retention elements 700 extending into the cavity from side wall 30.

FIG. 7A, a schematic drawing of a top down view (looking into the cavity formed by side walls and end walls) of cap housing member 10. As shown in the schematic cross sectional diagrams of FIGS. 7B-D (taken along line 7B-7B of FIG. 7A), the retention elements 700 serve to retain membrane 50 in proximity to the first major surface 41 of end wall 40. Space is shown between retention elements 700 and membrane 500 in FIGS. 7B-C. When the cap assembly is disposed about and tightened onto a cell culture vessel, a portion of the vessel may serve to push on membrane 50 to seal membrane against the first major surface 41 of the end wall 40 (similar to that shown in FIG. 10C). However, it will be understood that cap housing member 10 can be designed such that membrane 50 is disposed between first major surface 41 of end wall 40 and retaining features 700 via an interference fit. Of course, membrane may be adhered to first major surface 41 of end wall 40 to seal membrane 50 relative to the end wall 40 or may be sealed by any other suitable mechanism. Regardless of the mechanism, membrane 50 sealingly divides the major cavity 500 formed by end wall 40 and side wall 30 into a chamber 510 and a minor cavity 520. In the depicted embodiment, the chamber 510 is formed substantially by the counter bore 45 in the end wall 40. Filter 60 (not shown in FIGS. 7A-C) may be seated in counter bore 45. The filter may be adhered or otherwise form a seal with end wall 40 to ensure that air flowing through opening 15 passes through the filter. A space is preferably provided between the filter and the membrane 50 to allow sufficient room for membrane 50 to distend and allow slit 55 to open when a threshold pressure differential exists across the membrane 50.

Figure 8A:
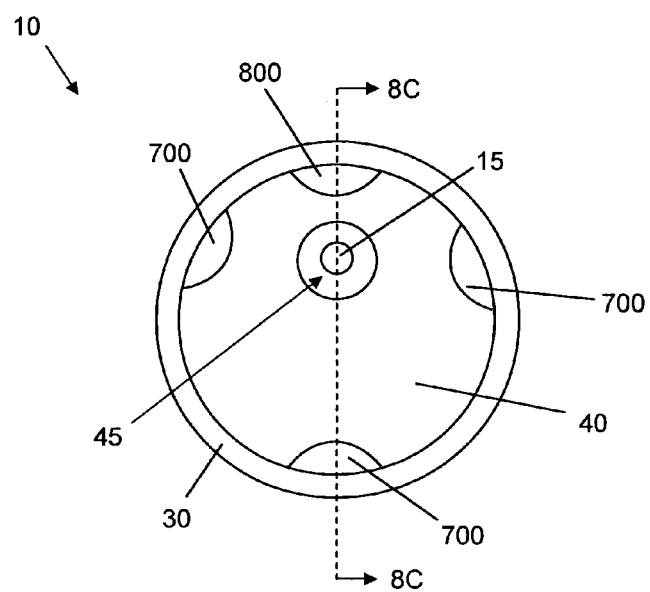
FIG. 8A is a schematic diagram of a top down view of a vent cap housing member looking into a cavity formed by a side wall and end wall of the housing member.
Figure 8B:
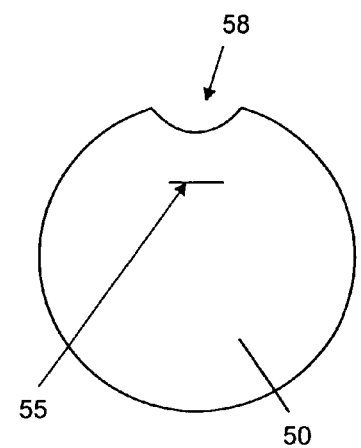
FIG. 8B is a schematic diagram of a top view of a membrane.
Figure 8C:
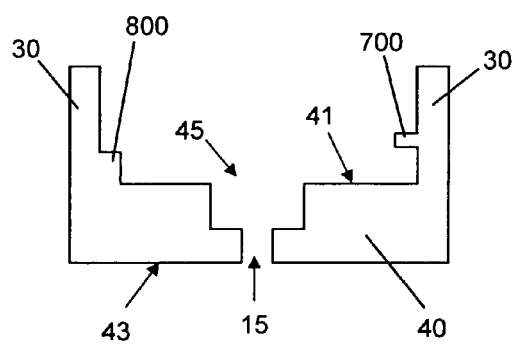
FIG. 8C is a schematic diagram of a cross section of the vent cap housing member shown in FIG. 8A taken along line 8C-8C.
Figure 8D:
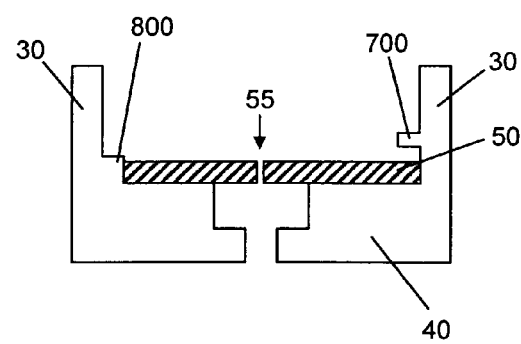
FIG. 8D is a schematic diagram a cross section of the vent cap housing member shown in FIG. 8C with a membrane.
Figure 9A:
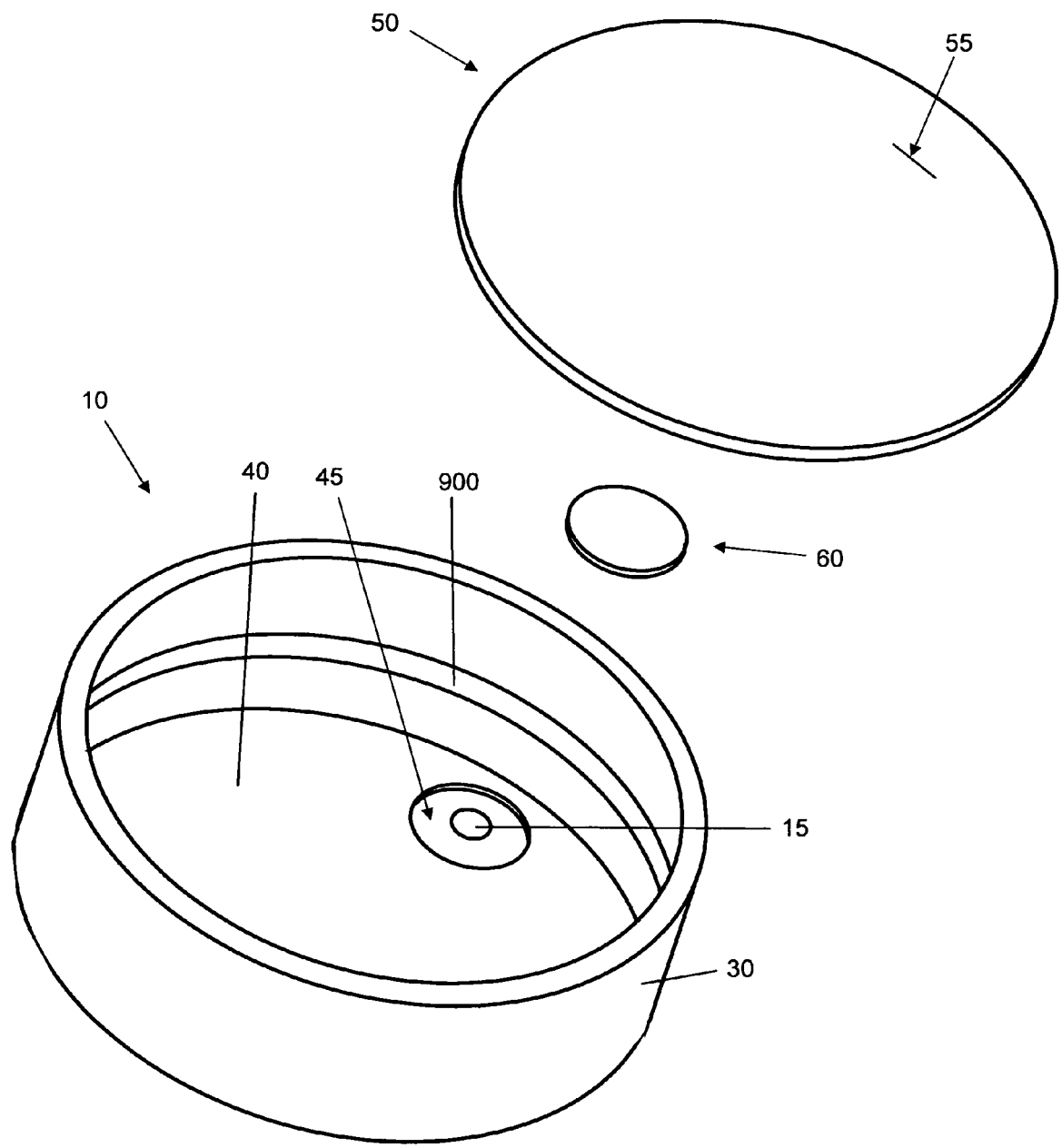
FIG. 9A is a schematic diagram of an exploded perspective view of a vent cap assembly.
Figure 9B:
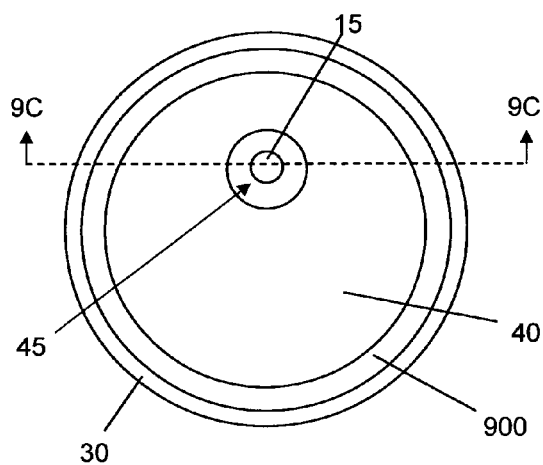
FIG. 9B is a schematic diagram of a top down view of the vent cap housing member shown in FIG. 9A looking into a cavity formed by a side wall and end wall of the housing member.
Figure 9C:
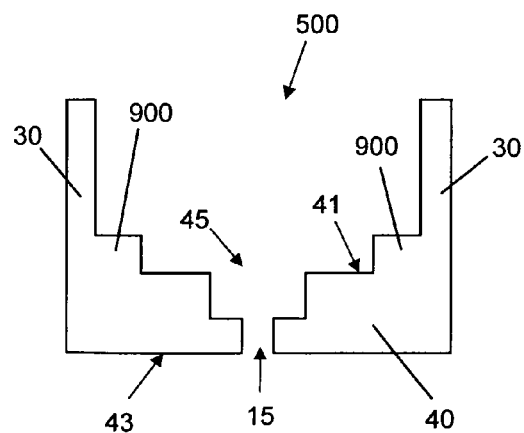
FIG. 9C is a schematic diagram of a cross section of the vent cap housing member shown in FIG. 9B taken along line 9C-9C.
Figure 9D:
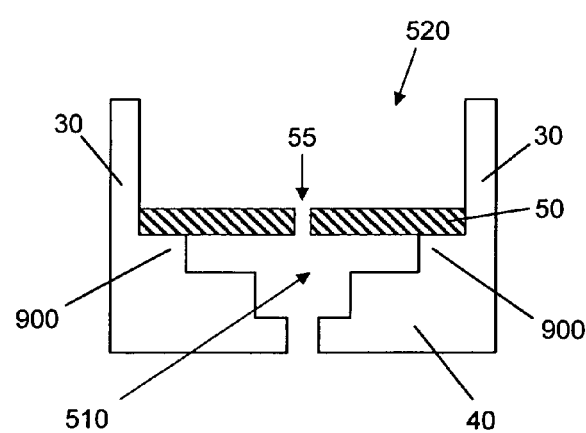
FIG. 9D is a schematic diagram a cross section of the vent cap housing member shown in FIG. 9C with a membrane.

As shown in FIGS. 8A-B, vent cap housing member 10 may have an alignment feature 800 such as a detent and membrane 50 may have a complementary alignment feature 58 such as an indent. The alignment features 800, 58 serve to keep slit 55 of membrane 50 in alignment with opening 15, counter bore 45, or other feature of housing member 10 to allow for sufficient space for membrane 50 to distend to allow slit 55 to open such that gas may pass through slit 55 and out opening 15. Feature 800 and complementary feature 58 may be of any suitable shape. As shown in FIGS. 8C-D, membrane 50 engages alignment feature 800 to align slit 55 with opening 15 and counter bore 45, providing sufficient space for membrane to distend into counter bore 45 to allow slit 55 to open. A filter (not shown) may be disposed in counter bore 45.

Referring now to FIG. 9, a vent cap assembly having a seat 900 extending inwardly from the side wall 30 of the vent cap housing 10 is shown. The seat 900 is configured to engage the membrane 50 such that the membrane 50 may sealingly divide the major cavity 500 into a chamber 510 and a minor cavity 520. The seat 900 also can serve to provide sufficient space between the membrane 50 and the end wall 40 to allow the membrane to distend, allowing slit 55 to open, when a sufficient pressure differential exists across the membrane 50. The membrane 50 may be sealed to the seat 900 via adhesive, via pressure from cell culture vessel (similar to that shown in FIG. 10C), via interference fit with retention elements (not shown in FIG. 9), or any other suitable mechanism. A filter 60 (not shown in FIGS. 9B-D) may be disposed in the counter bore 45.

Figure 10A:
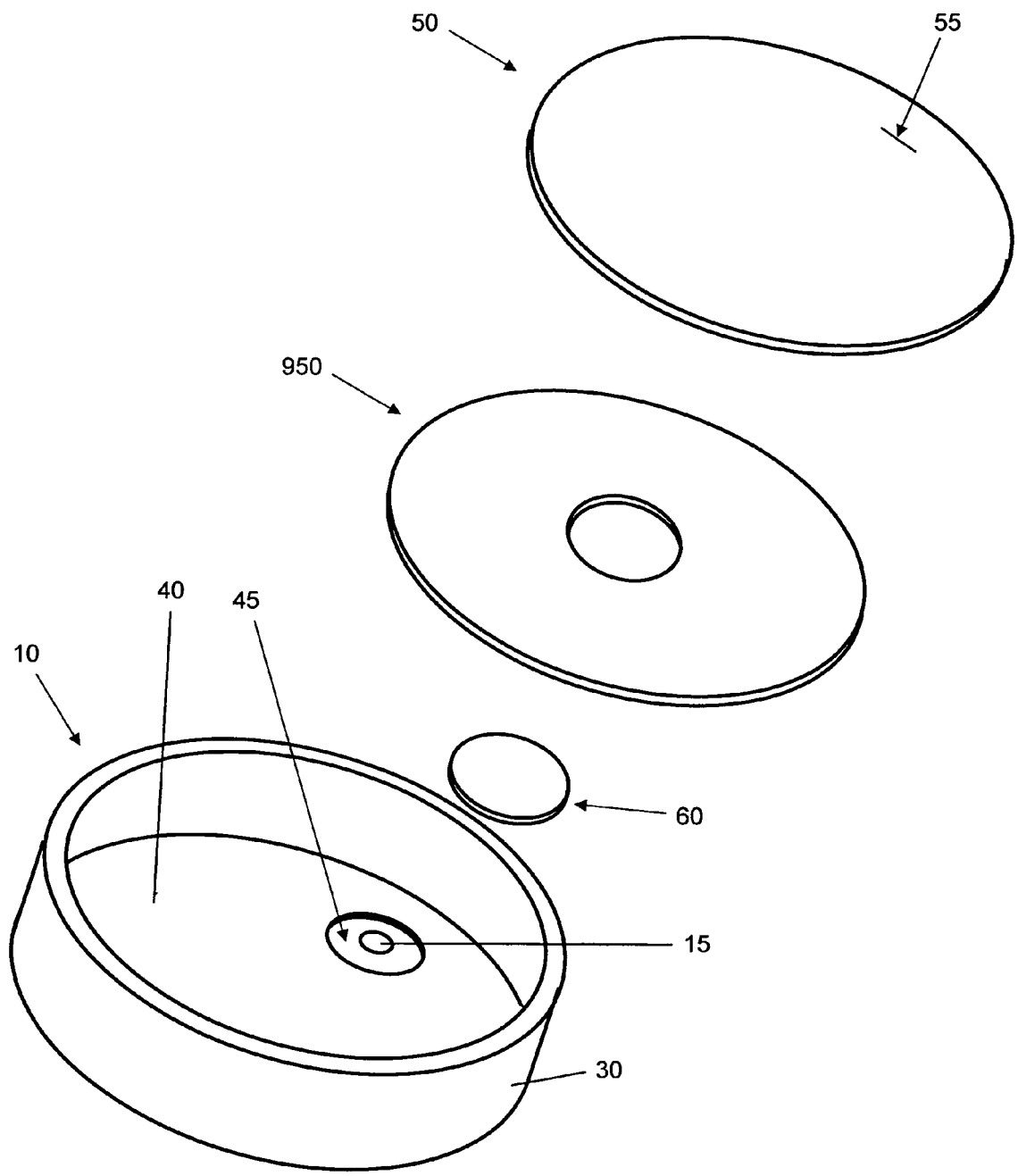
FIG. 10A is a schematic diagram of an exploded perspective view of a vent cap assembly.
Figure 10B:
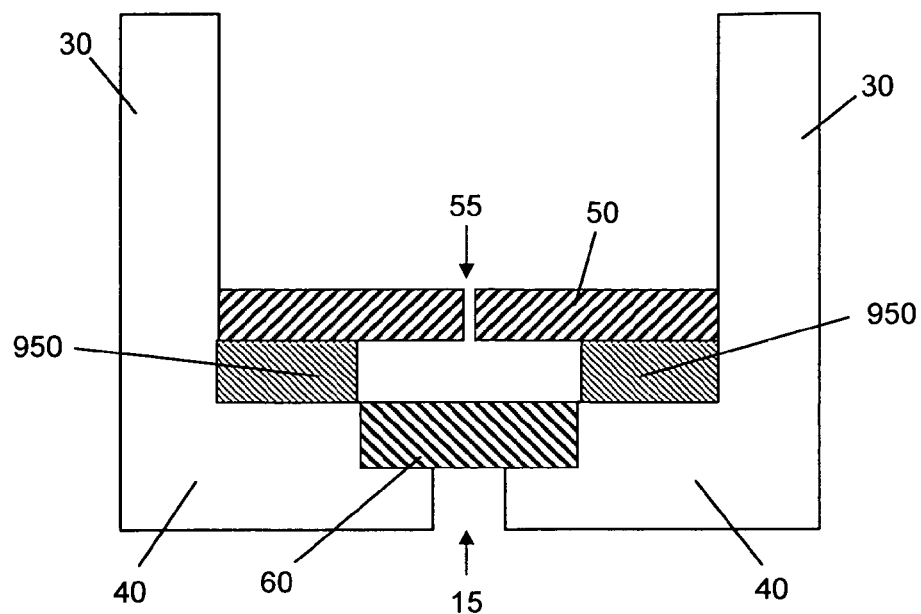
FIG. 10B is a schematic diagram of a cross section of the vent cap assembly shown in FIG. 10A.

Referring now to FIG. 10A-B, a vent cap assembly having a spacer member 950 such as an o-ring is shown. The spacer 950 in the depicted embodiment is configured to engage the membrane 50 and the end wall 40 such that the membrane 50 may sealingly divide the major cavity into a chamber 510 and a minor cavity 520. The spacer 950 also can serve to provide sufficient space between the membrane 50 and the end wall 40 to allow the membrane to distend, allowing slit to open, when a sufficient pressure differential exists across the membrane 50. A filter 60 may be sealingly disposed within the counter bore 45.

Figure 10C:
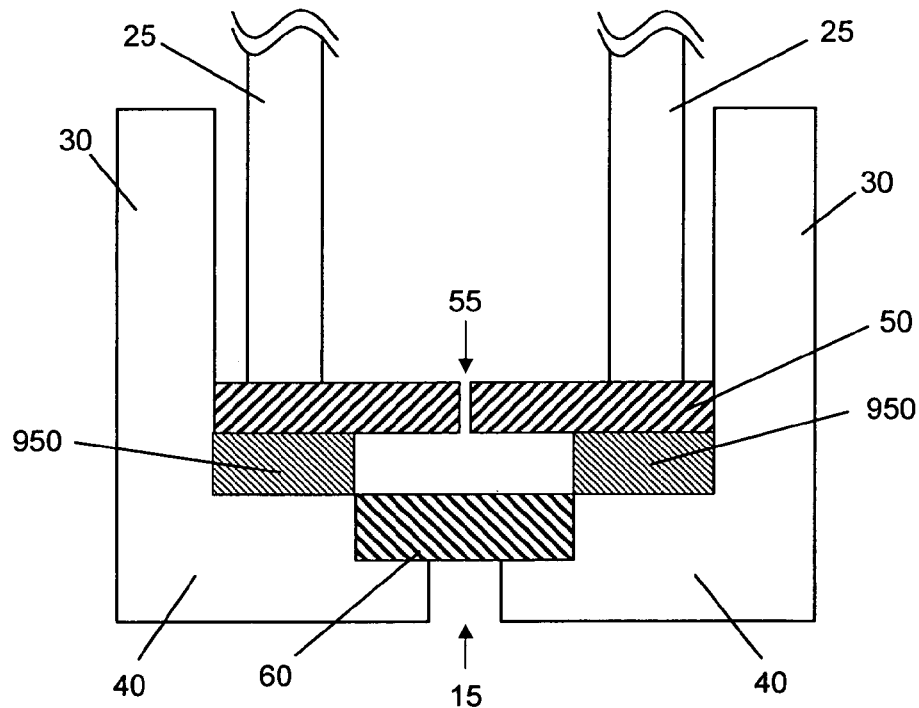
FIG. 10C is a schematic diagram a cross section of the vent cap housing member shown in FIG. 10B disposed about a neck region of a cell culture vessel.

As shown in FIG. 10C, the vent cap housing 10 may be disposed about a neck portion 25 of a cell culture vessel. As the vent cap assembly is tightened to the neck region 25 of the vessel (e.g. by screwing along threads (not shown)), the neck 25 may engage the membrane 50 and sealingly press membrane 50 against spacer 950 and sealing press spacer 950 against end wall 40. Of course, membrane 50 may be sealed relative to space 950 or spacer 950 may be sealed relative to end wall 40 via adhesive, via interference fit, or any other suitable mechanism.

Figure 11A:
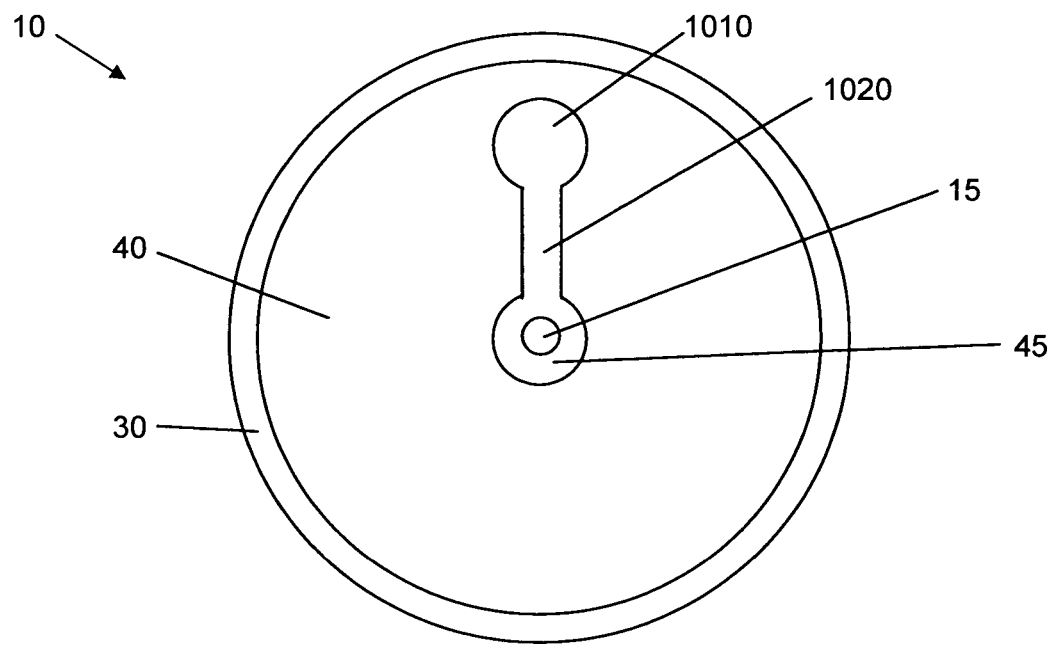
FIG. 11A is a schematic diagram of a top down view of a vent cap housing member looking into a cavity formed by a side wall and end wall of the housing member.
Figure 11B:
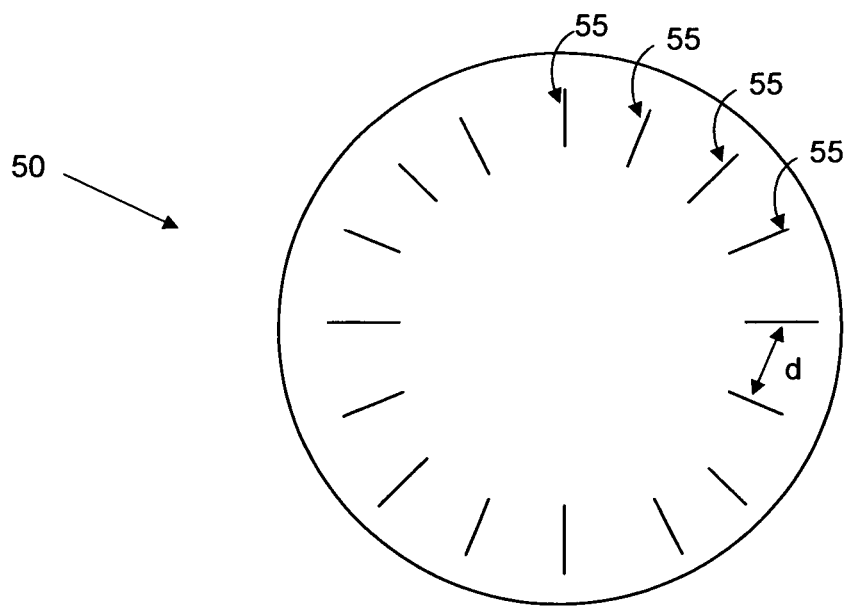
FIG. 11B is a schematic diagram of a top view of a membrane.
Figure 11C:
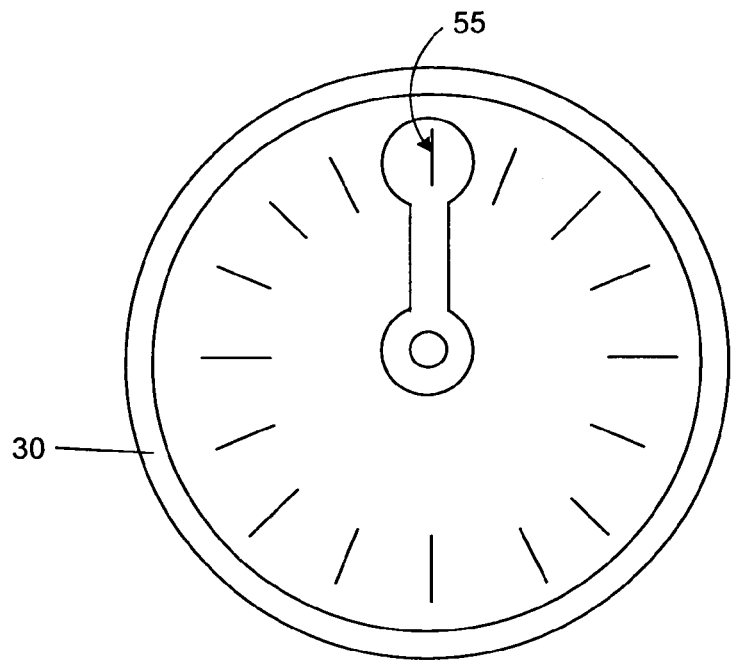
FIG. 11C is a schematic diagram of a top down view of the vent cap housing member shown in FIG. 11A looking into a cavity formed by a side wall and end wall of the housing member, with the membrane of FIG. 11B being disposed with in the cavity.

Referring to FIG. 11, an alternative mechanism for aligning a slit 55 of a membrane 50 with an appropriate portion of a vent cap housing member 10 is shown. In FIG. 11A, a vent cap housing member 10 includes a first counter bore 45 and a second counter bore 1010 in an end wall 40. The first 45 and second 1010 counter bores are connected via a channel 1020, and an opening 15 in the end wall 15 is disposed within an area of the end wall 40 in which the first counter bore 45 is formed. Referring to FIG. 11B, a membrane 50 has a plurality of radially spaced apart slits 55. The depicted slits 55 are substantially equally spaced apart at a distance d. FIG. 11C shows the membrane 50 (transparent) disposed with in the cap housing member 10 and on the end wall 40. When the diameter of the second counter bore 1010 is greater than the distance d between the slits 55 in the membrane 50. The membrane 50, slits 55, cap housing 10 and second counter bore 1010 are configured such that regardless of the orientation of the membrane 50 within relative to the counter bore 45, a slit 55 of the membrane 50 is aligned with the second counter bore 45. The second counter bore 1010 serves to provide space to allow the membrane to distend and allow slit 55 to open for venting. Vented fluid may then pass through channel 1020 to first counter bore 45 and out opening 15. A filter may be disposed within the first counter bore 45.

Figure 12A:
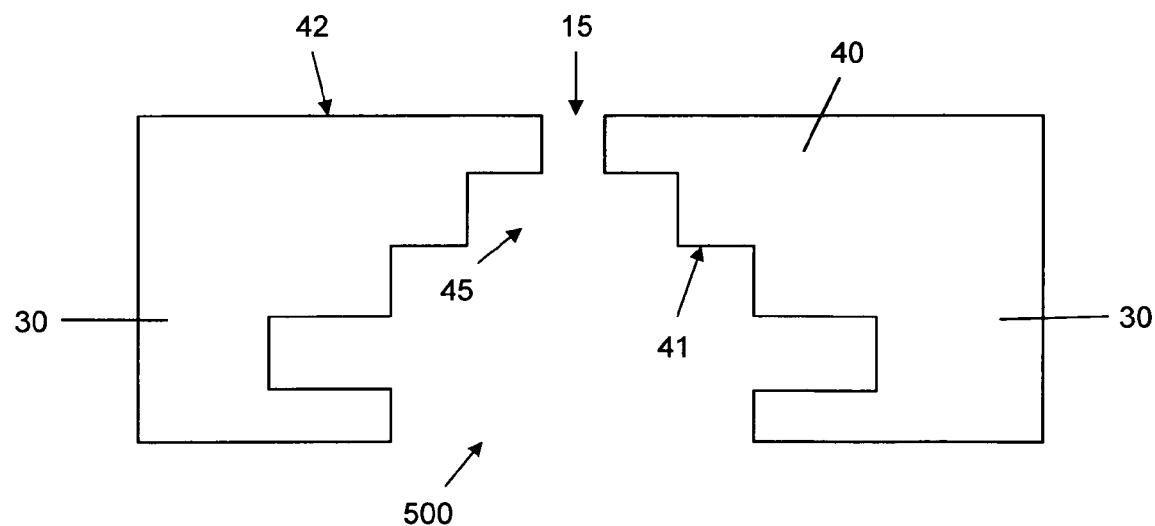
FIGS. 12A-C are schematic diagrams of a cross sections of a housing vent assembly.
Figure 12B:
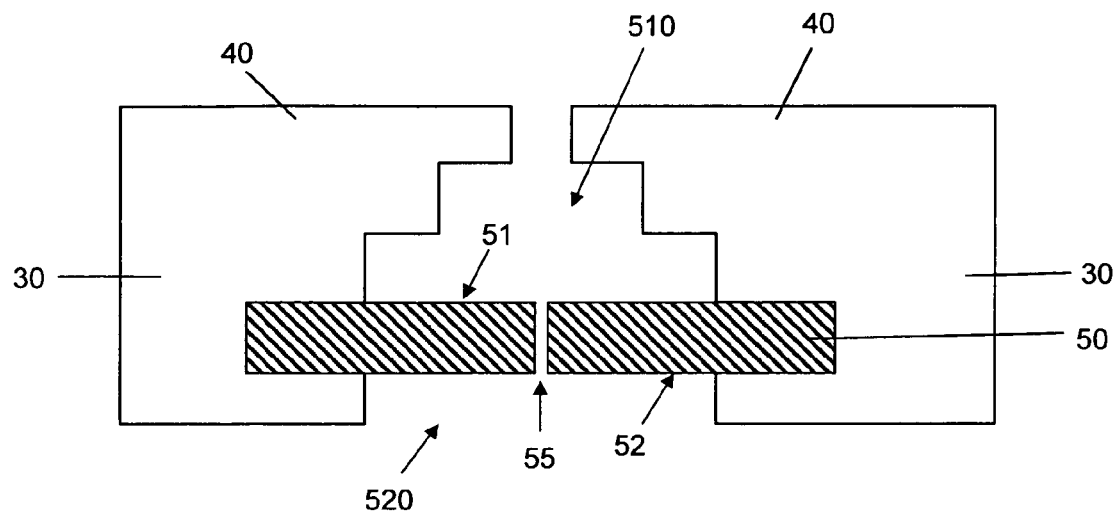
Figure 12C:
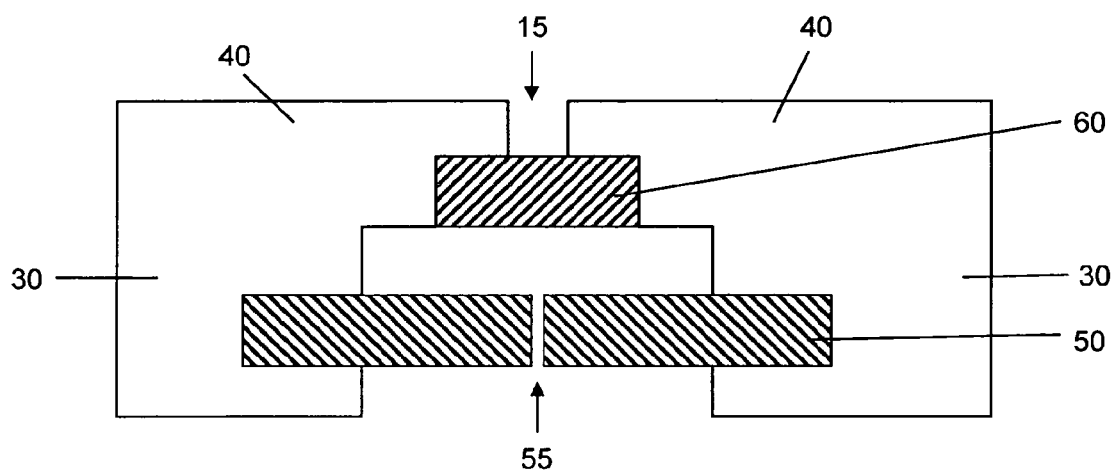

Referring now to FIGS. 12A-C, a valve assembly other than a vent cap assembly is shown. By way of example, the valve assembly may be an assembly as depicted in FIGS. 4A-B. The valve assembly depicted in FIGS. 12A-C includes a contiguous side wall 30 and an end wall 40 extending across one end of the side wall 30. The side wall 30 and the end wall 40 form a major cavity 500. A membrane 50 may be disposed within the major cavity 500 and may sealingly divide the cavity into a chamber 510 and a minor cavity 520. A filter 60 may be disposed in a counter bore 45 formed in the end wall 40 such that the air passing through the opening 15 passes through the filter 15. The vent cap assembly depicted in FIG. 12 is configured to sealingly engage an opening of a cell culture vessel, which opening is in fluid communication with a reservoir of the vessel. In various embodiments, the side wall 30 or side wall 30 and end wall 40 of the vent assembly are integrally formed with the housing of the cell culture vessel.

It will be understood that components and aspects of the various embodiments described herein may be interchanged. For example, the alignment feature described with regard to FIG. 8 may readily be incorporated into a vent cap housing having a seat as described with FIG. 9.

For the various embodiments described herein, it will also be understood that various components may be integrally formed or may be formed from separate parts. For example, a cap housing member may have a side wall integrally formed with an end wall or an end wall may be fastened or adhered to a side wall, or the like. Regardless of whether integrally formed or formed from separate parts, components, particularly those that may come in contact with cell culture medium, are preferably made of material that is not toxic to cells being cultured.

For example, a cell culture vessel housing may be formed from material including a ceramic substance, glass, or plastic. Suitable glass materials include soda-lime glass, pyrex glass, vycor glass, and quartz glass. Suitable plastics or polymers include, poly(vinyl chloride), poly(methyl methacrylate), poly(dimethylsiloxane) monomethacrylate, cyclic olefin polymers, fluorocarbon polymers, polystyrenes, polyethylene, polycarbonate, polyester, polypropylene; copolymers such as poly(styrene-co-maleic anhydride), poly(ethylene-co-acrylic acid), derivatives of these or the like. Many of such materials may allow for exchange of gasses from the reservoir to outside the vessel (and vice-versa). While such materials can be formed to be useful for exchange of gasses for purposes of cell culture, the rate at which gas can cross such materials may not be sufficient to vent gas during spikes in pressure.

Any suitable material, such as metallic materials, glass materials, or plastic or polymer materials, may be use to form cap or vent assembly housing components. One example of a suitable material is polyethylene.

A membrane as described herein may be made of any suitable flexible material. For example, a membrane may be formed from a polymer such as an elastomeric polymer. Examples of polymers that may be used to make a flexible filter include, polyethylene, polypropylene, polydimethylsiloxane, or a mixture of in-situ cross linking of ethylene-propylene-diene monomer rubber and polypropylene. If a material such as Santoprene™ is used to form membrane, it may be desirable to provide a backing of, e.g., polyester to increase stiffness and lubricity. Another example of a suitable material for forming a flexible membrane is foamed polypropylene. A membrane may have any thickness that allows the slit to open and close under desired pressure differentials across the membrane. By way of example, a membrane may have a thickness of between about 0.02 and 0.06 inches, or about 0.04 inches.

A filter as described herein preferably prevents passage of particles having an average diameter or diametric dimension of between about 0.1 and about 0.3 microns. For example, the filter may be what is typically referred to as a 0.2 micron filter. The filter may include a prefilter layer. For example, the prefilter layer may be configured to prevent the passage of particles having an average diametric dimension of between about 80 micrometers and about 120 micrometers. The filter may be formed from hydrophobic material to lower the possibility of aqueous liquid, such as culture media, from passing through the filter. For example, the filter may be formed from polytetrafluoroethylene, polyvinylidene fluoride, or polypropylene.

Thus, embodiments of FLEXIBLE MEMBRANE VALVE FOR CELL CULTURE ASSEMBLY are disclosed. One skilled in the art will appreciate that the arrays, compositions, kits and methods described herein can be practiced with embodiments other than those disclosed. The disclosed embodiments are presented for purposes of illustration and not limitation.

What is claimed is:

1. A vent cap assembly for a cell culture apparatus, comprising:
    a cap housing member having a generally cylindrical side wall and an end wall extending across one end of the side wall to form a major cavity within the cylindrical side wall and the end wall,
        wherein the end wall has a first major surface facing the major cavity, an opposing second major surface, and an opening extending through the end wall from the first major surface to the second major surface;
    a flexible membrane having first and second opposing major surfaces and a slit extending through the membrane from the first major surface to the second major surface,
        wherein the flexible membrane is disposable within the major cavity such that the membrane sealingly divides the major cavity into (i) a chamber formed between the first major surface of the end wall and the first major surface of the membrane and (ii) a minor cavity formed by the second major surface of the membrane and a portion of the side wall,
        wherein the slit is biased in a closed position to prevent fluid from passing from the minor cavity into the chamber and is configured to open to allow gas to pass from the minor cavity into the chamber when the pressure differential across the membrane is above a threshold; and
    a microbial filter disposed between the membrane and the opening such that air flowing through the opening in the end wall into the chamber passes through the filter.

2. The vent cap assembly of claim 1, further comprising a counter bore formed in the first major surface of the end wall and wherein the opening extends through the counter bore.

3. The vent cap assembly of claim 2, wherein the filter is disposed in the counter bore.

4. The vent cap assembly of claim 2, wherein the chamber is formed substantially by the counter bore.

5. The vent cap assembly of claim 1, further comprising a seat extending from the side wall into the cavity, wherein the first major surface of the flexible membrane is configured to sealingly engage the seat.

6. The vent cap assembly of claim 5, wherein the membrane is adhered to the seat.

7. The vent cap assembly of claim 1, further comprising a spacer disposed between the first major surface of the end wall and the first major surface of the membrane.

8. The vent cap assembly of claim 1, wherein the slit is positioned away from the center of the membrane.

9. The vent cap assembly of claim 8, wherein the opening is positioned away from the center of the end wall and is alignable with the slit of the membrane.

10. The vent cap assembly of claim 1, wherein the membrane contains a plurality of slits.

11. The vent cap assembly of claim 10, wherein the slits are positioned away from the center of the membrane and are substantially equally radially spaced apart at a first distance,
    wherein a counter bore having a diameter greater than the first distance is formed in the first major surface of the end wall, the counter bore being positioned away from the center of the end wall and being alignable with one or more of the slits, and
    wherein the end wall further comprises a channel formed in the first major surface, wherein the channel provides fluid communication from the counter bore to the opening.

12. A cell culture assembly comprising:
    a cell culture vessel having a housing defining a reservoir and a neck extending from the housing, the neck defining an opening in fluid communication with the reservoir; and
    the vent cap assembly of claim 1, wherein the cap housing member is configured to be disposed about the neck.

13. An assembly for culturing cells, comprising:
    a housing defining a reservoir for containing cell culture media and an opening in fluid communication with the reservoir; and
    a filter valve assembly configured to sealingly engage the opening to prevent gas from exiting the reservoir via the opening,
    wherein the filter valve assembly comprises the flexible membrane, a contiguous side wall, an end wall, and a microbial filter,
        wherein the end wall extends across one end of the side wall to form a major cavity within the side wall and the end wall,
        wherein the end wall has a first major surface facing the major cavity, an opposing second major surface, and an opening extending through the end wall from the first major surface to the second major surface,
        wherein the flexible membrane has first and second opposing major surfaces and a slit spanning the membrane from the first to the second major surface,
        wherein the flexible membrane is disposable within the major cavity such that the membrane sealingly divides the major cavity into (i) a chamber formed between the first major surface of the end wall and the first major surface of the membrane and (ii) a minor cavity formed by the second major surface of the membrane and a portion of the side wall, the minor cavity being in fluid communication with the reservoir, wherein the slit is biased in a closed position to prevent fluid from passing from the minor cavity into the chamber and is configured to open to allow gas to pass from the minor cavity into the chamber when the pressure differential across the membrane is above a threshold, and wherein the microbial filter is disposed between the membrane and the opening such that air flowing through the opening in the end wall into the chamber passes through the filter.

14. The assembly of claim 13, wherein the filter valve assembly further comprises a seat extending from the side wall into the cavity, wherein the first major surface of the flexible membrane is configured to sealingly engage the seat.

15. The assembly of claim 13, wherein the filter valve assembly further comprises a spacer disposed between the first major surface of the end wall and the first major surface of the membrane.

16. The assembly of claim 13, wherein the housing further comprises a neck, wherein the neck defines the opening.

17. The assembly of claim 16, wherein the filter valve assembly is a vent cap configured to be disposed about the neck.

18. The assembly of claim 13, wherein the side wall of the filter valve assembly is integrally formed with the housing such that the side wall defines the opening.

19. The assembly of claim 13, wherein the housing is gas permeable.

* * * * *